US00PP24735P2

(12) United States Plant Patent
Hanes

(10) Patent No.: US PP24,735 P2
(45) Date of Patent: Aug. 5, 2014

(54) *PELARGONIUM* PLANT NAMED 'PEQZ0001'

(50) Latin Name: ***Pelargonium* spp.**
Varietal Denomination: PEQZ0001

(75) Inventor: Mitchell Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 112 days.

(21) Appl. No.: 13/507,847

(22) Filed: Aug. 2, 2012

(51) Int. Cl.
*A01H 5/00* (2006.01)

(52) U.S. Cl.
USPC ..... Plt./324

(58) Field of Classification Search
USPC ..... Plt./324, 325, 332, 329
See application file for complete search history.

(56) References Cited

U.S. PATENT DOCUMENTS

PP15,616 P2 * 3/2005 Hanes ..... Plt./324
PP20,245 P2 * 9/2009 Hanes ..... Plt./324
PP20,896 P2 * 3/2010 Hanes ..... Plt./329

OTHER PUBLICATIONS

PLUTO: Plant Variety Database, citation of *pelargonium* plnat named 'PEQZ0001' (CH PBR 10-2700) filed Dec. 16, 2010, denomination and application published Jan. 31, 2011, and denomination published Apr. 30, 2011). (https://www3.wipo.int/pluto/user/en/index.jsp) Dec. 4, 2013.*

* cited by examiner

*Primary Examiner* — Susan McCormick Ewoldt
(74) *Attorney, Agent, or Firm* — Joshua L. Price

(57) ABSTRACT

A new *Pelargonium* plant named 'PEQZ0001' particularly distinguished by the large mostly semi-double bright red-purple inflorescences, medium green foliage, good garden performance growing well in both sun and shade, with lateral plant habit, excellent branching and zonal like foliage.

1 Drawing Sheet

Latin name of the genus and species of the plant claimed: *Pelargonium* spp.

Varietal denomination: 'PEQZ0001'.

BACKGROUND OF THE NEW PLANT

The present invention comprises a new *Pelargonium*, botanically known as *Pelargonium* spp., and hereinafter referred to by the variety name 'PEQZ0001'.

'PEQZ0001' is a product of a planned breeding program. The new cultivar 'PEQZ0001' has large mostly semi-double bright red-purple inflorescences, medium green foliage, good garden performance growing well in both sun and shade, with lateral plant habit, excellent branching and zonal like foliage.

'PEQZ0001' originates from a hybridization in a controlled breeding program in February 2007 in Gilroy, Calif. The female parent was a proprietary plant identified as 'Amri Pur', U.S. Plant Pat. No. 20,896, with violet-purple colored flowers that are smaller and a more upright habit when compared to 'PEQZ0001'.

The male parent of 'PEQZ0001' was a the proprietary plant identified as 'Cante Dereds', U.S. Plant Pat. No. 15,616, with single deep red flowers and more ivy-type foliage and habit when compared to 'PEQZ0001'. The resultant seed was sown in a greenhouse in August 2007 in Gilroy, Calif.

'PEQZ0001' was selected as one flowering plant within the progeny of the stated cross in December 2007 in a greenhouse in Gilroy, Calif.

The first act of asexual reproduction of 'PEQZ0001' was accomplished when vegetative cuttings were propagated from the initial selection in December 2007 in a greenhouse in Gilroy, Calif.

BRIEF SUMMARY OF INVENTION

Horticultural examination of plants grown from cuttings of the plant initiated in December 2007 in Gilroy, Calif., and continuing thereafter, has demonstrated that the combination of characteristics as herein disclosed for 'PEQZ0001' are firmly fixed and are retained through successive generations of asexual reproduction.

'PEQZ0001' has not been observed under all possible environmental conditions. The phenotype may vary significantly with variations in environment such as temperature, light intensity, and day length.

Plant Breeder's Rights for this cultivar were applied for in Canada on Nov. 1, 2011, No. 11-7416 and in Switzerland on Dec. 16, 2010, No. 2012-2700. 'PEQZ0001' has not been made publicly available more than one year prior to the filing of this application.

The following traits have been repeatedly observed and are determined to be basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0001' with colors being as true as possible with an illustration of this type.

Figure 1:
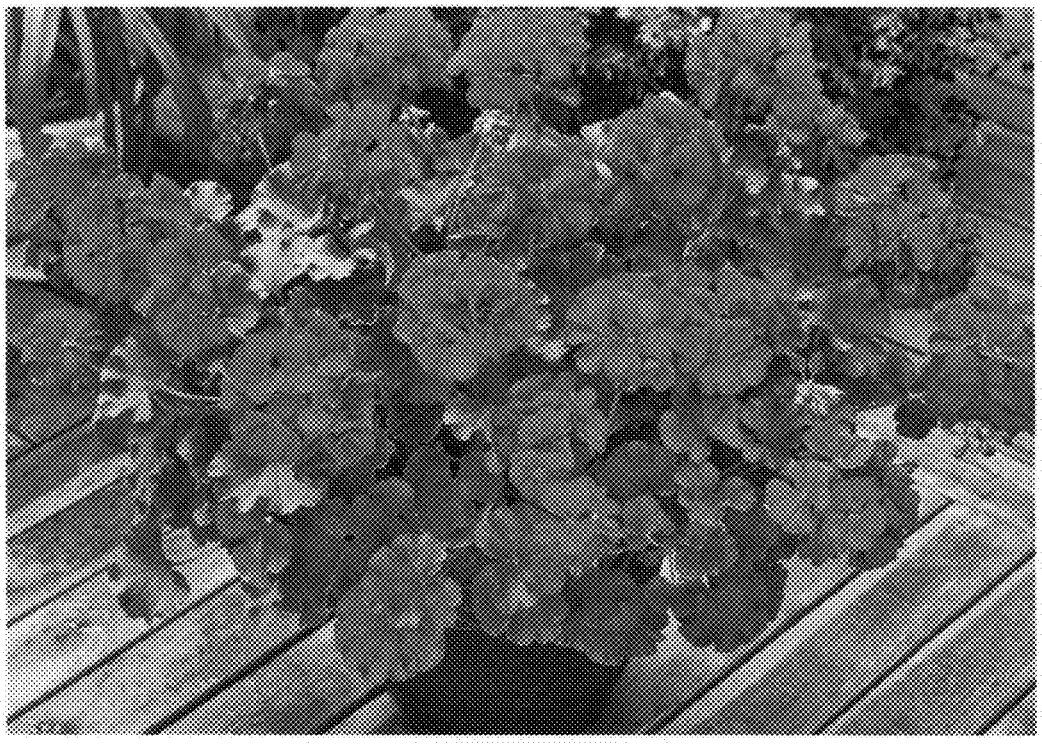
Figure 2:
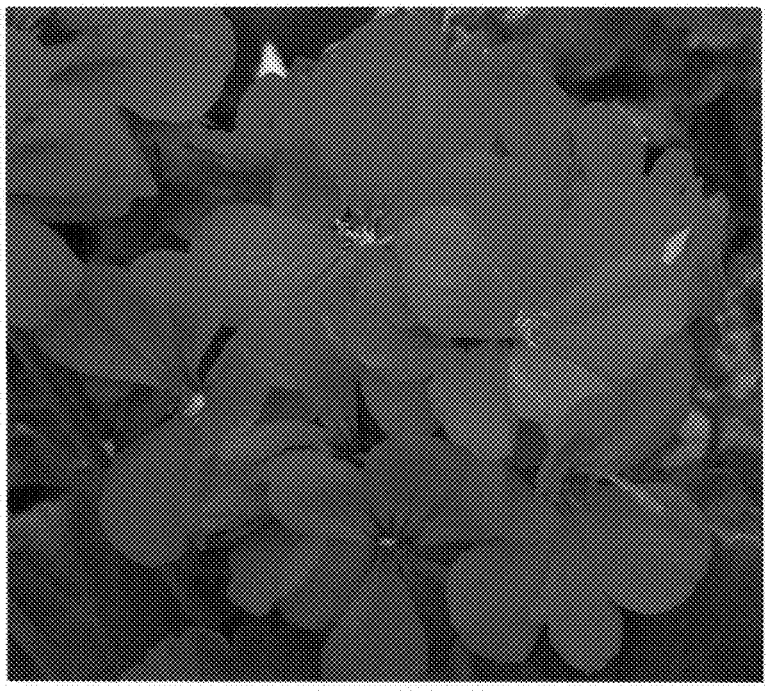

The photographic drawing shows in FIG. 1, 3 flowering plants of the new variety, and in FIG. 2, a close-up of an inflorescence.

DETAILED BOTANICAL DESCRIPTION

The plant descriptions and measurements were taken in Gilroy, Calif. under natural light in late May 2012. These plants were approximately 17-19 weeks old and were grown in 1 gallon pots in a greenhouse trial. The plants shown in the photographs were about 25 weeks old growing in a 10 inch pot in a greenhouse. The photographs were taken in April 2012.

Color Chart used: Royal Horticultural Society Colour Chart (R.H.S.) 2001

TABLE 1

DIFFERENCES BETWEEN THE NEW VARIETY 'PEQZ0001' AND A MOST SIMILAR VARIETY FOR PLANT TYPE

| | 'PEQZ0001' | 'Amri Trared' (U.S. Plant Pat. No. 20,245) |
|---|---|---|
| Floret size: | Larger | Smaller |
| Floret color: | Red-purple | Red |
| Plant habit size: | Larger | Smaller |
| Floriferousness: | More | Less |

TABLE 2

DIFFERENCES BETWEEN THE NEW VARIETY 'PEQZ0001' AND A MOST SIMILAR VARIETY FOR FLOWER COLOR

| | 'PEQZ0001' | 'Cante Ros' (U.S. Plant Pat. No. 15,834) |
|---|---|---|
| Floret type: | Semi-double | Single |
| Pedicel anthocyanins: | Present | Absent |
| Peduncle length: | Shorter | Longer |
| Pollen color: | Lighter orange | More red-orange |

Plant:

*Form, growth and habit.*—Upright, outwardly spreading and rounded growth habit. Vigorous, well branched, and grows well in sun or semi-shade.

*Plant height.*—14-17.0 cm.

*Plant height (inflorescence included).*—25-27.0 cm.

*Plant width.*—40-45.0 cm.

Roots:

*Number of days to initiate roots.*—13-17 days at about 22 degrees C.

*Number of days to produce a rooted cutting.*—21-24 days at 22 degrees C.

*Type.*—Fine, fibrous, free branching.

*Color.*—RHS N155B but whiter.

Foliage:

*Immature leaf, color upper surface.*—Inner half of leaf is closest to RHS 137C with the outer half closest to RHS 137A.

*Immature leaf, lower surface.*—Closest to RHS 146A.

*Mature leaf, color upper surface.*—Inner half of leaf is closest to RHS 137C with the outer half closest to RHS 137A, but darker intensities than the immature foliage.

*Mature leaf, color lower surface.*—Closest to RHS146A.

*Length.*—4.5-5.0 cm.

*Width.*—7.9-8.3 cm.

*Shape.*—Orbicular.

*Base shape.*—Cordate.

*Apex shape.*—Rounded.

*Margin.*—Crenate.

*Texture upper side.*—Hirsute.

*Texture lower side.*—Hirsute.

*Color of veins, upper surface.*—Closest to RHS 144A.

*Color of veins, lower surface.*—Closest to RHS 144A.

*Pattern of veining.*—Palmate.

*Petiole color.*—Closest to RHS 144A.

*Petiole length.*—5-9.0 cm.

*Diameter of petiole.*—0.3 cm.

*Texture.*—Hirsute.

Stem:

*Quantity of branches.*—8-10.

*Color of stem.*—Closest to RHS 144A.

*Length of stem.*—15-20.0 cm.

*Diameter.*—0.5-0.8 cm.

*Length of internodes.*—0.5-1.0 cm.

*Texture.*—Hirsute, pilose.

Peduncle:

*Color of peduncle.*—Closest to RHS 144A.

*Length of peduncle.*—13-14.0 cm.

*Peduncle diameter.*—0.3 cm.

*Texture.*—Hirsute, pilose, glandular hairs that have a little anthocyanin within them.

Pedicel:

*Color of pedicel.*—Varying shades of RHS 184A.

*Length of pedicel.*—3-3.5 cm.

*Diameter of pedicel.*—0.15 cm.

*Texture.*—Hirsute, pilose, glandular hairs that have anthocyanin within them.

Bud (just before opening):

*Color.*—Between RHS 46A and RHS 46B.

*Length.*—1.5-1.7 cm.

*Width.*—0.7-0.9 cm.

*Shape.*—Elliptical.

Inflorescence:

*Type.*—An umbel, semi-spherical or nearly semi-spherical.

*Lastingness of individual flowers.*—7-9 days at 18° C. temperature.

*Number of inflorescences per plant.*—21-24 umbels with open florets, and 10-12 with only buds.

*Number of flowers per inflorescence.*—Approximately 20-30.

*Fragrance.*—None.

*Umbel diameter.*—12-14.0 cm.

*Umbel depth.*—6-7.0 cm.

Corolla:

*Form.*—Semi-double.

*Number of petals.*—6-9.

*Diameter of flower.*—5.7-6.0 cm.

*Depth of flower.*—1.5-2.0 cm.

*Color upper petals, upper surface.*—Closest to RHS N57A with RHS 60A veining.

*Color upper petals, lower surface.*—RHS 58B.

*Length of upper petals.*—3.1-3.2 cm.

*Width of upper petals.*—1.8-2.0 cm.

*Color lower petals, upper surface.*—Closest to RHS N57A with slightly darker veining.

*Color lower petals, lower surface.*—RHS 58B.

*Length of lower petals.*—2.9-3.0 cm.

*Width of lower petals.*—1.8-2.2 cm.

*All petals.*—

*Petal shape.*—Broadly obovate.

*Apex shape.*—Rounded.

*Margin.*—Entire.

*Base.*—Cuneate.

*Petal texture.*—Papillose.

*Number of petaloids.*—0-3.

*Color of petaloids.*—Same as mature petals.

*Shape*.—Same as mature petals.

*Average width*.—0.8 cm.

*Average length*.—1.5 cm.

Calyx:

*Number of sepals*.—5.

*Color of sepals*.—Between RHS 144B and RHS 144C.

*Length of sepals*.—1.0-1.1 cm.

*Width of sepals*.—0.2-0.4 cm.

*Sepal shape*.—Lanceolate.

*Apex shape*.—Acute.

*Margins*.—Entire.

*Texture*.—Pilose, hirsute, glandular hairs with anthocyanin within them.

Reproductive organs:

*Gynoecium*.—Pistil: 1. Length: 1.2 cm. Style color: RHS 47B that is slightly darker basally. Style length: 0.7 cm. Stigma color: RHS 47B. Ovary color: RHS 144B covered with white hairs. Ovary length: 0.6 cm. Ovary diameter: 0.2 cm.

*Androecium*.—Number of anthers: About 8; sometimes with a few extra filaments that aren't fully formed with anthers, or formed into petaloids. Color of filaments: RHS N155C with RHS 51A on the upper half and RHS 53D apex. Length filaments: 0.6 cm. Anther color: About RHS 32B. Length of anthers: 0.15 cm. Color of pollen: RHS N25B to RHS N25C. Pollen amount: Normal. Fertility/seed set: Little to no seed set observed. Disease/Pest Resistance: Has not been observed to date.

What is claimed is:

1. A new and distinct variety of *Pelargonium* plant named 'PEQZ0001' substantially as illustrated and described herein.

* * * * *